US00PP26668P2

(12) United States Plant Patent
Smith

(10) Patent No.: US PP26,668 P2
(45) Date of Patent: Apr. 26, 2016

(54) DENDRANTHEMA PLANT NAMED 'SIZZLING IGLOO'

(50) Latin Name: *Chrysanthemum×morifolium*
Varietal Denomination: Sizzling Igloo

(71) Applicant: Mark A. Smith, Fort Myers, FL (US)

(72) Inventor: Mark A. Smith, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 140 days.

(21) Appl. No.: 13/998,707

(22) Filed: Nov. 26, 2013

(51) Int. Cl.
*A01H 5/02* (2006.01)

(52) U.S. Cl.
USPC ..... Plt./295

(58) Field of Classification Search
USPC ..... Plt./295, 289
See application file for complete search history.

*Primary Examiner* — Keith Robinson
(74) *Attorney, Agent, or Firm* — C. A. Whealy

(57) ABSTRACT

A new and distinct cultivar of *Dendranthema* plant named 'Sizzling Igloo', characterized by its upright, outwardly spreading and uniformly mounded plant habit; freely branching habit; dense and full plant form; uniform and freely flowering habit; daisy-type inflorescences; bright yellow-colored ray florets; and good garden performance and winter hardiness.

1 Drawing Sheet

Botanical designation: *Chrysanthemum×morifolium.*
Cultivar denomination: 'SIZZLING IGLOO'.

BACKGROUND OF THE INVENTION

The present invention relates to a new and distinct *Dendranthema* plant, botanically known as *Chrysanthemum×morifolium*, commercially grown as a perennial garden-type *Dendranthema* plant, and hereinafter referred to by the cultivar name 'Sizzling Igloo'.

The objective of the breeding program is to create new perennial garden-type *Dendranthema* plants having uniformly mounding plant habit, inflorescences with desirable inflorescence forms, attractive floret colors and good winter hardiness and garden performance.

The new *Dendranthema* plant originated from a cross-pollination made by the Inventor in September, 2006, in Bogota, Colombia of a proprietary selection of *Chrysanthemum×morifolium* identified as code number P1558, not patented, as the female, or seed, parent with *Chrysanthemum×morifolium* 'Yogwendolyn', disclosed in U.S. Plant Pat. No. 17,533, as the male, or pollen, parent. The new *Dendranthema* plant was discovered and selected by the Inventor as a single flowering plant within the progeny of the stated cross-pollination in a controlled greenhouse environment in Alva, Fla. on Oct. 26, 2007.

Asexual reproduction of the new *Dendranthema* plant by vegetative cuttings was first conducted in a controlled greenhouse environment in Alva, Fla. in January, 2008 and such asexual propagation has shown that the unique features of this new *Dendranthema* plant are stable and reproduced true to type in successive generations.

SUMMARY OF THE INVENTION

Plants of the new *Dendranthema* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Sizzling Igloo'. These characteristics in combination distinguish 'Sizzling Igloo' as a new and distinct garden-type *Dendranthema* plant:

1. Upright, outwardly spreading and uniformly mounded plant habit.
2. Freely branching habit; dense and full plant form.
3. Uniform and freely flowering habit.
4. Daisy-type inflorescences.
5. Bright yellow-colored ray florets.
6. Natural season flowering occurs about September 20 to 23 in the Northern Hemisphere.
7. Good garden performance and winter hardiness.

In side-by-side comparisons, plants of the new *Dendranthema* differ from plants of the female parent selection in the following characteristics:

1. Plants of the new *Dendranthema* are larger than plants of the female parent selection.
2. Plants of the new *Dendranthema* flower about two weeks later than plants of the female parent selection when grown under natural season conditions.
3. Plants of the new *Dendranthema* have larger inflorescences than plants of the female parent selection.

In side-by-side comparisons, plants of the new *Dendranthema* differ from plants of the male parent, 'Yogwendolyn', in the following characteristics:

1. Plants of the new *Dendranthema* flower about two weeks later than plants of 'Yogwendolyn' when grown under natural season conditions.
2. Plants of the new *Dendranthema* and 'Yogwendolyn' differ in ray floret color as plants of 'Yogwendolyn' have white-colored ray florets.

Plants of the new *Dendranthema* can be compared to plants of *Chrysanthemum×morifolium* 'Yohankie', disclosed in U.S. Plant Pat. No. 16,929. In side-by-side comparisons, plants of the new *Dendranthema* differ from plants of 'Yohankie' in the following characteristics:

1. Plants of the new *Dendranthema* flower about ten days earlier than plants of 'Yohankie'.
2. Plants of the new *Dendranthema* have smaller inflorescences with more ray florets than plants of 'Yohankie'.

BRIEF DESCRIPTION OF THE PHOTOGRAPHS

The accompanying photographs illustrate the overall appearance of the new *Dendranthema* showing the colors as true as it is reasonably possible to obtain in colored reproductions of this type. Colors in the photographs may differ slightly from the color values cited in the detailed botanical description which accurately describe the colors of the new *Dendranthema* plant.

The photograph at the bottom of the sheet comprises a side perspective view of a typical flowering plant of 'Sizzling Igloo' grown in a container.

The photograph at the top of the sheet is a close-up view of typical inflorescences of 'Sizzling Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type *Dendranthema* production. During the production of the plants, day temperatures averaged 27.8° C. and night temperatures averaged 15.6° C. Plants were 19 weeks old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Sizzling Igloo'.

Parentage:

*Female, or seed, parent*.—Proprietary selection of *Chrysanthemum×morifolium* identified as code number P1558, not patented.

*Male, or pollen, parent*.—*Chrysanthemum×morifolium* 'Yogwendolyn', disclosed in U.S. Plant Pat. No. 17,533.

Propagation:

*Type*.—Terminal vegetative cuttings.

*Time to initiate roots*.—About four days at temperatures about 21° C.

*Time to produce a rooted young plant*.—About ten to twelve days at temperatures about 21° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching, dense.

Plant description:

*Plant and growth habit*.—Perennial garden-type *Dendranthema* plant with daisy-type inflorescences; upright, outwardly spreading and uniformly mounding plant habit; strong and vigorous growth habit.

*Branching habit*.—Freely branching habit, about seven primary lateral branches each with multiple secondary and tertiary branches; dense and full plant form; pinching is not required.

*Plant height*.—About 34 cm.

*Plant width*.—About 56 cm.

*Lateral branches*.—Length: About 27 cm. Diameter: About 4 mm. Internode length: About 1.7 cm. Strength: Strong. Texture: Pubescent; longitudinally ridged. Color: Close to 147B.

*Leaves*.—Arrangement: Alternate, simple. Length: About 3 cm. Width: About 2.4 cm. Apex: Broadly acute. Base: Attenuate. Margin: Palmately lobed, sinuses between lateral lobes mostly parallel and medium. Texture, upper and lower surfaces: Pubescence; veins prominent on lower surface. Luster, upper and lower surfaces: Matte. Venation pattern: Pinnate. Color: Developing and fully expanded leaves, upper surface: Close to 147A; venation, close to 147B. Developing and fully expanded leaves, lower surface: Close to 147B; venation, close to 147C. Leaf petioles: Length: About 1.1 cm. Diameter: About 2 mm.

Aspect: Somewhat upright. Texture, upper and lower surfaces: Pubescent. Color, upper surface: Close to 148B. Color, lower surface: Close to 148C.

Inflorescence description:

*Type and arrangement*.—Daisy-type inflorescence form with ligulate-shaped ray florets; disc and ray florets arranged acropetally on a capitulum; inflorescences face mostly upright and held above the foliar plane on strong peduncles.

*Fragrance*.—Faintly fragrant, sour.

*Flowering response*.—Under natural season conditions, plants flower about September 20 to 23 in the Northern Hemisphere.

*Postproduction longevity*.—Inflorescences maintain good color and substance for about six weeks on the plant; inflorescences persistent.

*Quantity of inflorescences*.—Freely flowering habit with about 95 inflorescences developing per lateral branch.

*Inflorescence buds*.—Height: About 9 mm. Diameter: About 1.2 cm. Shape: Oblate, flat-topped. Color: Close to 13A.

*Inflorescence size*.—Diameter: About 3.5 cm. Depth (height): About 1.4 cm. Disc diameter: About 1.1 cm. Receptacle diameter: About 1.6 cm. Receptacle height: About 6 mm. Receptacle color: Close to 147B.

*Ray florets*.—Quantity and arrangement: About 45 ray florets develop per inflorescence and arranged in about two to three whorls. Length: About 1.6 cm; length of fused portion, about 5 mm. Width: About 6 mm. Shape: Ligulate. Apex: Emarginate, minutely tri-dentate. Base: Attenuate. Margin: Entire. Orientation: Initially upright, then about 90° from vertical; apices angled slightly upright. Texture, upper and lower surfaces: Smooth, glabrous; velvety; longitudinally ribbed. Color: When opening, upper surface: Close to 15A. When opening, lower surface: Close to 13A. Fully opened, upper surface: Close to 13B; color does not fade with development. Fully opened, lower surface: Close to 12C; color does not fade with development.

*Disc florets*.—Quantity and arrangement: About 120 fused disc florets develop per inflorescence and massed at the center of the capitulum. Length: About 7 mm. Diameter: About 1 mm. Shape: Tubular, elongated. Apex: Five-pointed. Texture, inner and outer surfaces: Smooth, glabrous. Color, immature: Apex: Close to 15A. Mid-section: Close to 145C. Base: Close to 145D. Color, mature: Apex: Close to 13B. Mid-section: Close to 145C. Base: Close to 145D.

*Phyllaries*.—Quantity and arrangement: About 24 phyllaries develop per inflorescence and arranged in about two to 2.5 whorls. Length: About 5 mm. Width: About 3 mm. Shape: Elliptical. Apex: Acute. Base: Truncate. Margin: Entire; membraneous. Texture, upper surface: Smooth, glabrous. Texture, lower surface: Pubescent. Color, upper surface: Close to 146A. Color, lower surface: Close to 146B to 146C.

*Peduncles*.—Length, terminal peduncle: About 9.6 cm. Length, fourth peduncle: About 5.4 cm. Diameter, terminal peduncle: About 1.5 mm. Angle: Mostly upright or curving upright. Strength: Strong. Texture: Pubescent. Color: Close to 148C.

*Reproductive organs*.—Androecium (present on disc florets only): Stamen number: Five per floret. Filament length: About 2.5 mm. Filament color: Close to 1C. Anther length: About 2 mm. Anther shape: Narrowly oblong. Anther color: More dull than 15A. Pollen amount: Scarce. Pollen color: Close to 13A. Gynoecium (present on ray and disc florets): Pistil length: About 6 mm. Stigma shape: Bi-parted. Stigma color: Close to 3C. Style length: About 5 mm. Style color: Close to 145C. Ovary color: Close to 155A.

*Seeds and fruits*.—Seed and fruit production has not been observed on plants of the new *Dendranthema*.

Disease & pest resistance: Resistance to pathogens and pests common to *Dendranthema* plants has not been observed on plants grown under commercial production conditions.

Garden performance & temperature tolerance: Plants of the new *Dendranthema* have demonstrated excellent garden performance, are hardy to USDA Zone 5 and tolerate high temperatures of about 37.8° C.

It is claimed:

1. A new and distinct *Dendranthema* plant named 'Sizzling Igloo' as illustrated and described.

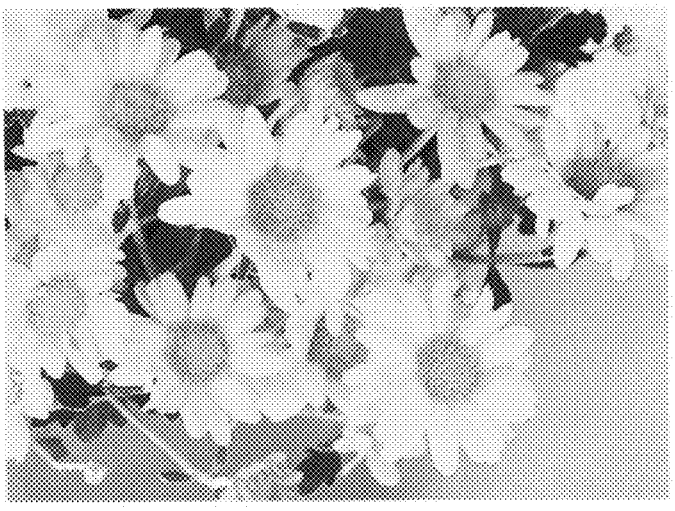
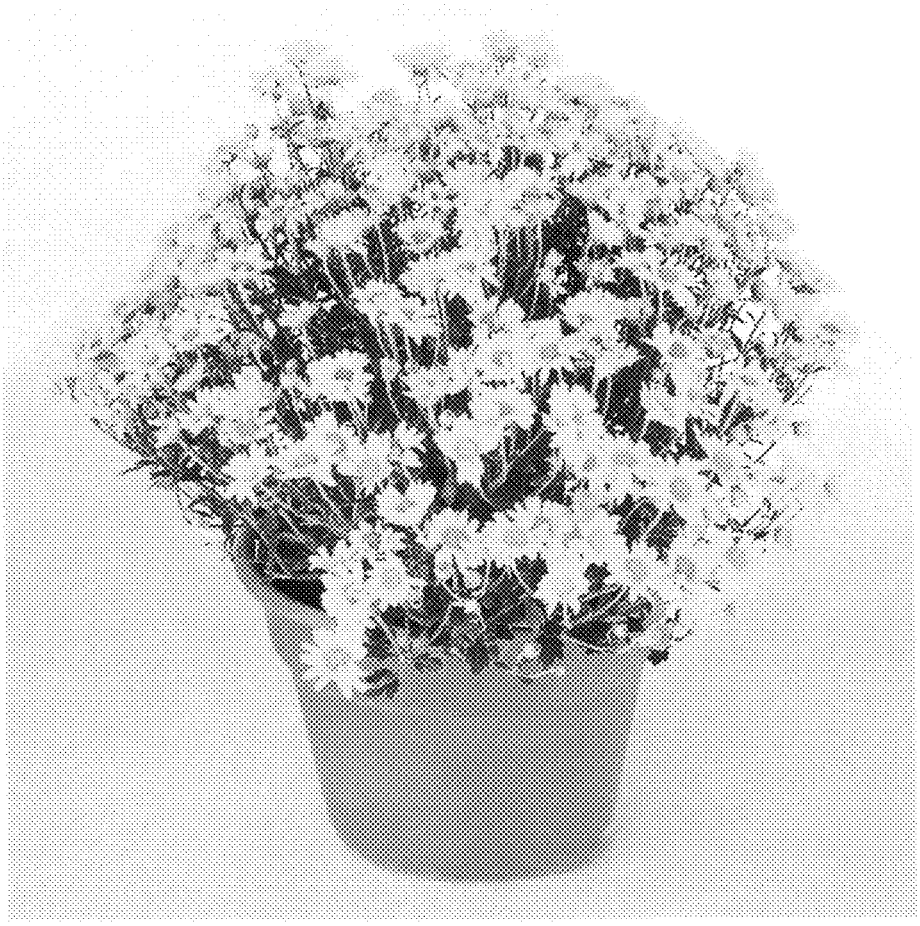

* * * * *